United States Patent
Reinen et al.

(10) Patent No.: US 12,045,694 B2
(45) Date of Patent: Jul. 23, 2024

(54) BUILDING A MODEL BASED ON RESPONSES FROM SENSORS

(71) Applicant: INTERNATIONAL BUSINESS MACHINES CORPORATION, Armonk, NY (US)

(72) Inventors: Jenna Reinen, Greenwich, CT (US); Aldis Sipolins, New York, NY (US); Patrick Watson, Montrose, NY (US); Ravi Tejwani, Cambridge, MA (US); Marco Cavallo, New York, NY (US); Hui Wu, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 629 days.

(21) Appl. No.: 16/448,176

(22) Filed: Jun. 21, 2019

(65) Prior Publication Data
US 2020/0401933 A1    Dec. 24, 2020

(51) Int. Cl.
| | |
|---|---|
| *G06N 20/00* | (2019.01) |
| *G06F 3/01* | (2006.01) |
| *G16C 60/00* | (2019.01) |
| *H04L 67/50* | (2022.01) |

(52) U.S. Cl.
CPC ............. *G06N 20/00* (2019.01); *G06F 3/015* (2013.01); *G16C 60/00* (2019.02); *H04L 67/535* (2022.05)

(58) Field of Classification Search
CPC ......... G06N 20/00; H04L 67/22; G06F 3/015; G06F 1/163; G06T 19/006
See application file for complete search history.

(56) References Cited

U.S. PATENT DOCUMENTS

| | | |
|---|---|---|
| 5,697,791 A | 12/1997 | Nashner et al. |
| 6,546,397 B1 * | 4/2003 | Rempell ............... G06F 40/166 |
| 9,477,993 B2 | 10/2016 | Frank et al. |
| 9,569,812 B1 * | 2/2017 | Kopf .................. H04N 21/8146 |

(Continued)

OTHER PUBLICATIONS

Atterer et al., "Knowing the User's Every Move" published 2006, downloaded from https://www.researchgate.net/publication/221023546_Knowing_the_user's_every_move_User_activity_tracking_for_website_usability_evaluation_and_implicit_interaction (Year: 2006).*

(Continued)

*Primary Examiner* — Eric J Yoon
(74) *Attorney, Agent, or Firm* — Daniel Morris; Otterstedt & Kammer PLLC (57) ABSTRACT

A system includes a virtual reality system configured to enable a user to interact with a virtual environment, a plurality of biofeedback sensors configured to monitor a user, and a computer system including a virtual reality module configured to generate at least a view of the virtual environment, a biofeedback module configured to fuse output of the plurality of biofeedback sensors with a plurality of events within the virtual environment, a training module configured to generate a model of user behavior, wherein the training module executed by the computer system enables the computer system to make a prediction of a user response of the user based on a corpus of biofeedback data, and an alert module configured to generate at least one alert to the user via the virtual reality system based on the user response predicted by the computer system.

16 Claims, 6 Drawing Sheets

(56) References Cited

U.S. PATENT DOCUMENTS

| | | | |
|---|---|---|---|
| 2007/0173733 A1* | 7/2007 | Le | G16H 10/20 |
| | | | 600/544 |
| 2008/0318673 A1 | 12/2008 | Rofougaran | |
| 2015/0248615 A1 | 9/2015 | Parra et al. | |
| 2016/0255384 A1 | 9/2016 | Marci et al. | |
| 2016/0342905 A1 | 11/2016 | Ghose et al. | |
| 2019/0094966 A1* | 3/2019 | Kulkarni | G06F 1/163 |
| 2019/0198153 A1* | 6/2019 | Hill | A61B 5/375 |
| 2019/0228330 A1* | 7/2019 | Kaifosh | G06F 3/015 |
| 2020/0380540 A1* | 12/2020 | Fox | G06N 20/00 |

OTHER PUBLICATIONS

V. Dissanayake et al., "Real Time Gesture Prediction Using Mobile Sensor Data for VR Applications," International Journal of Machine Learning and Computing, vol. 6, No. 3, published Jun. 2016 (Year: 2016).*

* cited by examiner

BUILDING A MODEL BASED ON RESPONSES FROM SENSORS

BACKGROUND

The present disclosure relates generally to devices and methods employing machine learning, and more particularly to a device comprising sensors and employing machine learning for predicting a behavioral response.

BRIEF SUMMARY

According to one or more embodiments of the present invention, a closed loop machine learning system uses multiple biomarkers to predict behavior specific to an individual. According to at least one embodiment, a fused model of multiple sources of biofeedback data is created to drive closed-loop predictions in multiple interactive virtual and actual environments, where the closed-loop predictions are used to infer affective states from a user.

According to at least one embodiment of the present invention, a system includes a virtual reality system configured to enable a user to interact with a virtual environment, a plurality of biofeedback sensors configured to monitor a user, and a computer system including a virtual reality module configured to generate at least a view of the virtual environment, a biofeedback module configured to fuse output of the plurality of biofeedback sensors with a plurality of events within the virtual environment, a training module configured to generate a model of user behavior, wherein the training module executed by the computer system enables the computer system to make a prediction of a user response of the user based on a corpus of biofeedback data, and an alert module configured to generate at least one alert to the user via the virtual reality system based on the user response predicted by the computer system.

According to some embodiments, a method of constructing a predictive model for user behavior in a virtual environment comprises determining a baseline response for each of a plurality of sensors and a user, building an individualized model comprising a plurality of priors generated from the baseline responses, the individualized model configured to predict a response of the user based on a time-stamped stimulus presentation in the virtual environment, sampling, iteratively, responses of the user to respective events in the virtual environment during the time-stamped stimulus presentation, linking each of the responses and the respective events to an interval of time, and updating at least one of the priors of the individualized model based on linked ones of the responses and events.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments may provide for:

fusing multiple biofeedback data streams and using the biofeedback data streams to infer affective states from a user on a fine temporal scale (e.g., milliseconds);

linking the biofeedback data streams iteratively to behavioral outputs measured by a VR system, such as decision making, hand-eye-coordination, and responses to social interaction;

optimizing features that predict a behavioral response for a particular user on each iteration of the loop; and modifying or communicating with a VR system or environment using fused biofeedback data streams and affective states.

These and other features and advantages of the present invention will become apparent from the following detailed description of illustrative embodiments thereof, which is to be read in connection with the accompanying drawings.

BRIEF DESCRIPTION OF THE SEVERAL VIEWS OF THE DRAWINGS

Preferred embodiments of the present invention will be described below in more detail, with reference to the accompanying drawings.

DETAILED DESCRIPTION

Many decisions are linked to complex, instantaneous, and non-verbal processes. These processes can be difficult to measure and predict from biological measures of a user (e.g., biofeedback). Further, individuals have varying and dynamic responses to biological measures, making generalizations across users particularly noisy. In the context of a virtual reality (VR) environment in which users are monitored by biofeedback, and are likely to repeat behavior given time spent in a particular gaming or interactive context, a model that combines biofeedback loops with behavioral output to a VR setting is needed for developing models that may predict and hone individualized behavior based on these iterations.

According to one or more embodiments of the present invention, a closed-loop machine learning system uses multiple biomarkers to predict behavior specific to an individual.

According to at least one embodiment, a fused model of multiple sources of biofeedback data is created to drive closed-loop predictions in multiple virtual environments. According to some embodiments, the closed-loop machine learning system outputs the fused model for action or use by a VR system.

According to at least one embodiment, construction of an individual variability model with a closed loop design enables individual tuning, which improves on existing methods that pool variance across participants.

According to some embodiments of the present invention, a device comprising sensors samples biophysical changes of a user. The samples can be taken at prescribed times, for example, on a millisecond (ms) timescale. It should be understood that other timescales can be used.

Figure 1:
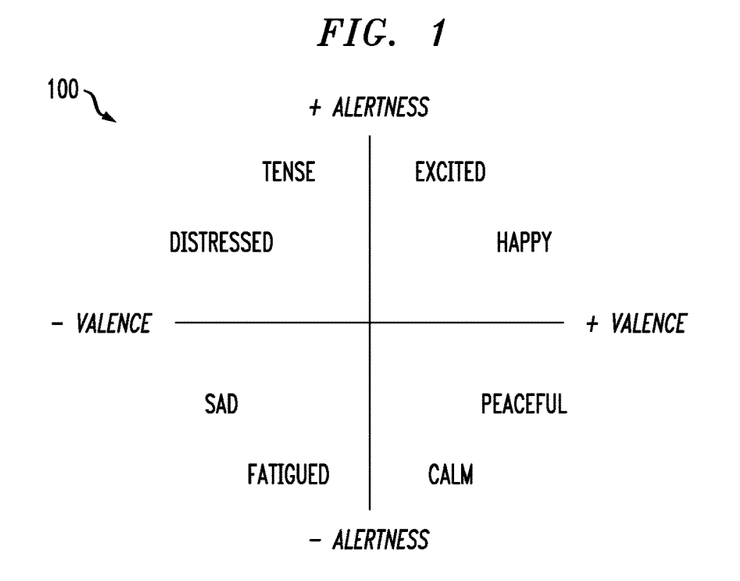
FIG. 1 depicts a spectrum of responses according to at least one embodiment of the present invention.

As described herein, the emotions that underlie decisions are detected. According to some embodiments of the present invention, emotion is used to predict decisions. As show in FIG. 1, emotions fall on a spectrum 100 of valence (positive and negative) and alertness. Different biosensors pick up different types of responses. In the case of alertness, parameters including eye tracking, heart rate, respiration, skin conductance, etc. can be used. In the case of valence, parameters including micro-expressions, self-reporting can be used. According to one or more embodiments of the present invention, the precision of a decision prediction can be improve using information related to collected information (i.e., from multiple biometric sources). For example, while being anxious and excited are different emotions, they recruit the same type of attention response. The difference between the emotions can be lost only alertness is measured (and not valence). Further, individuals respond differently to these metrics; according to at least one embodiment of the present invention, decision prediction is improved by coupling these measurements with a personalized machine learning system.

Figure 2:
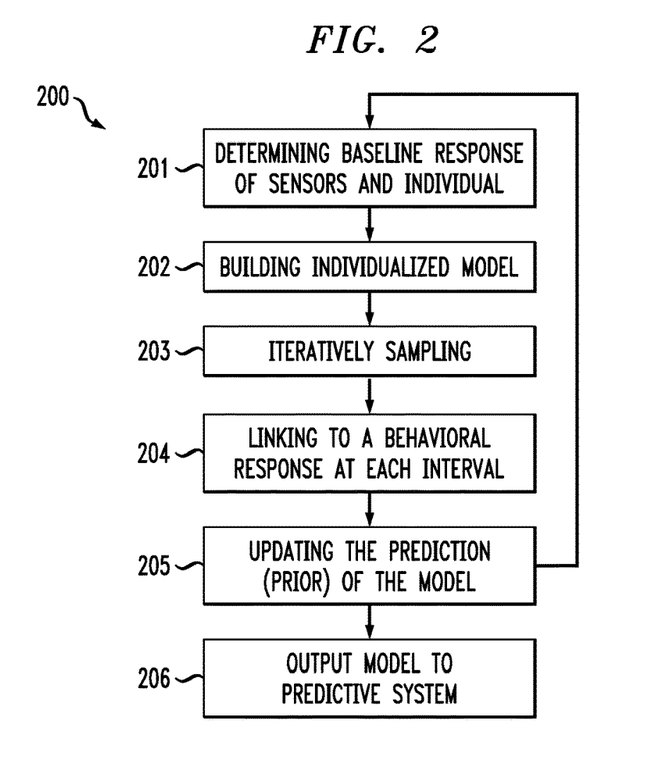
FIG. 2 depicts a closed-feedback loop according to at least one embodiment of the present invention.

According to at least one embodiment of the present invention, a method for building a predictive model 200 includes determining a baseline response for a plurality of sensors and an individual 201, and building an individualized model that predicts the individual's response based on a time-stamped stimulus presentation 202. According to some embodiments, the individualized model includes one or more priors, where a prior is related to a respective prediction. The individual responses can be, for example, to a product while watching a commercial, or to specific stimuli during an experiment. The method further includes iteratively sampling 203 to achieve highly accurate, individually-specific dynamic outputs of response to an experiences, and linking to a behavioral response at each interval 204. At block 204, the linking can establish, for example, whether a person makes a decision such as choosing to buy a product or not, or in another example, did a person correctly remember a particular stimulus. The method further includes updating the prediction (a prior) of the model based on the outcome 205. According to at least one embodiment, a prior gives a range of baseline features that are specific to an individual. For example, in a case of two different persons associated with respective heart rate measurements, while one individual may have a higher heart rate (on average), the variability in the heart rate of the given individual is used as the predictor in the moment, ignoring other metrics such as the mean. Thus, the prior can be used to ignore a (e.g., high) mean and focus on variability. According to some embodiments, the method includes an output of the model to a predictive system 206, such as an augmented reality (AR) maintenance manual that guides a user through a repair of an object or facility and includes a predictive functionality based on user behavior (e.g., predicting the intent of the user).

It should be understood that references to VR and AR systems herein are not limiting, and that references to either system are interchangeable with the other.

Figure 3:
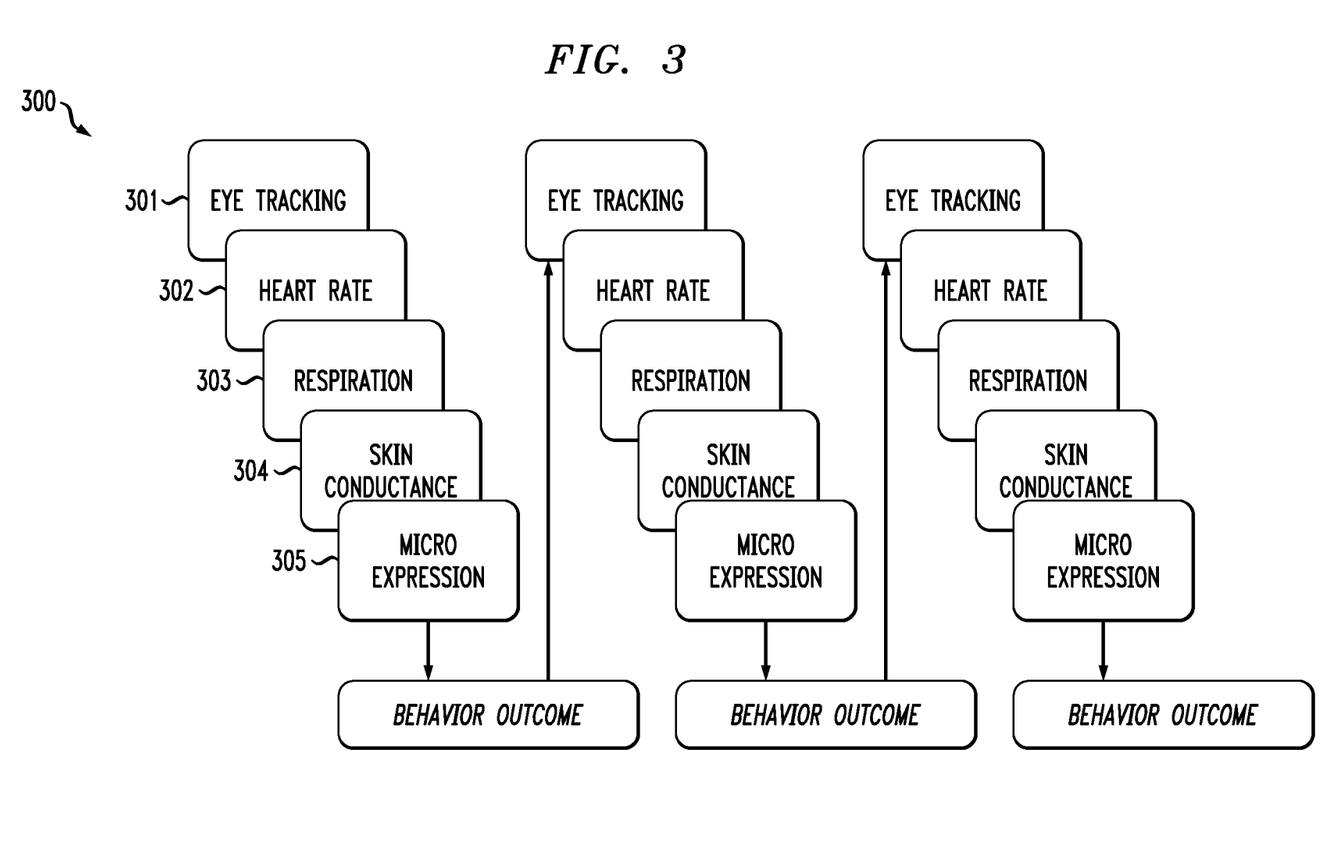
FIG. 3 depicts a range of predicted behaviors according to at least one embodiment of the present invention.

FIG. 3 shows an example of a closed-feedback loop 300. In the closed-loop, machine learning-based system, multiple sources of biofeedback data (301-305) are used to iteratively and adaptively learn what best predicts an individual's behavioral response.

Figure 4:
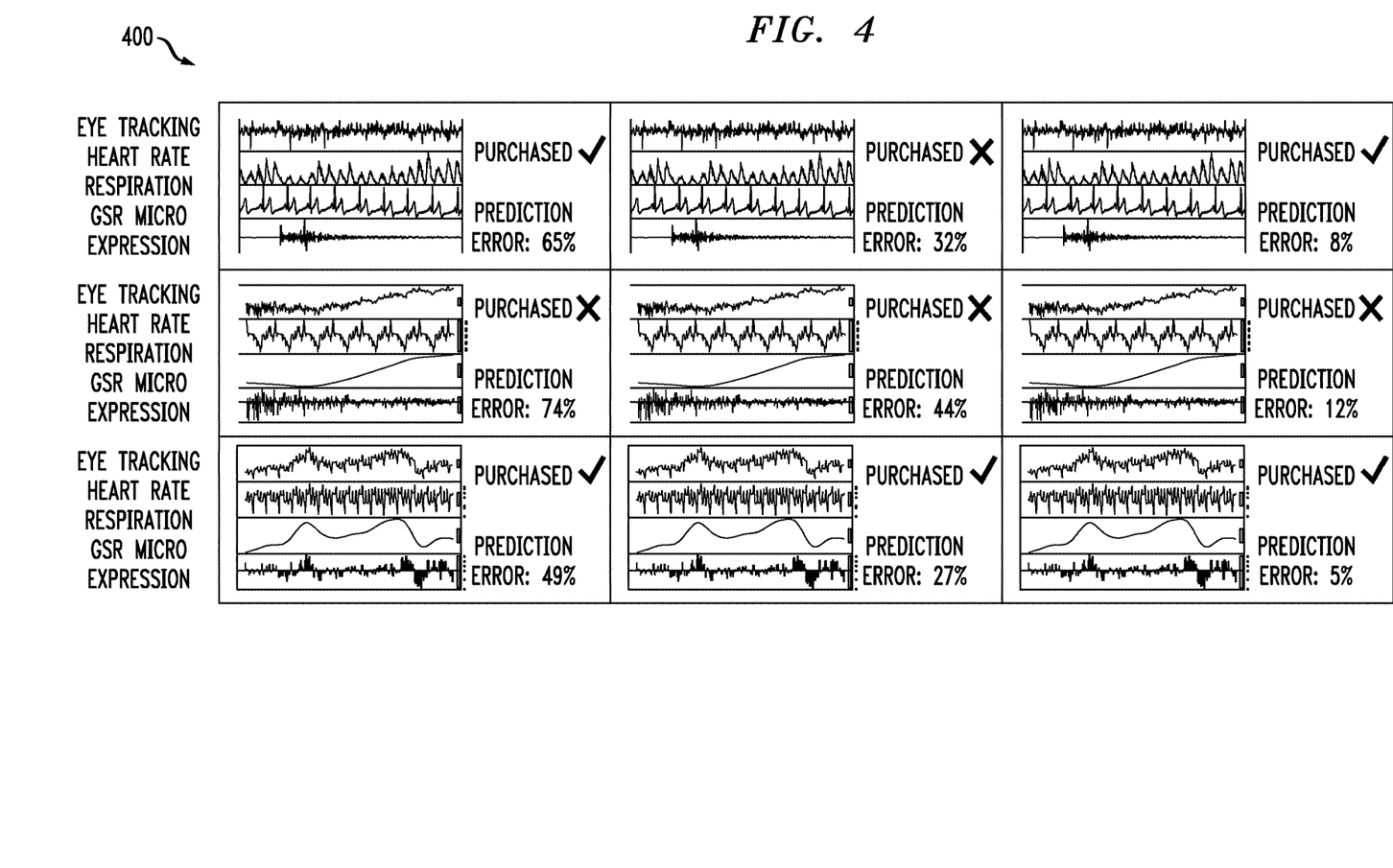
FIG. 4 depicts a range of predicted behaviors according to at least one embodiment of the present invention.

According to some embodiments of the present invention, biofeedback data 400 is shown in FIG. 4, wherein users have watched commercials and indicated with a button press when they decide they would like to purchase the product being shown. The biofeedback data is collected from sensors including an eye tracking system, heart rate monitor, respiration monitor, and galvanic skin response (GSR) monitor, and micro expression monitor. According to some embodiments of the present invention, the biofeedback data is the input to the machine learning system to predict behavior, cognitive responses and/or motor responses.

Figure 5:
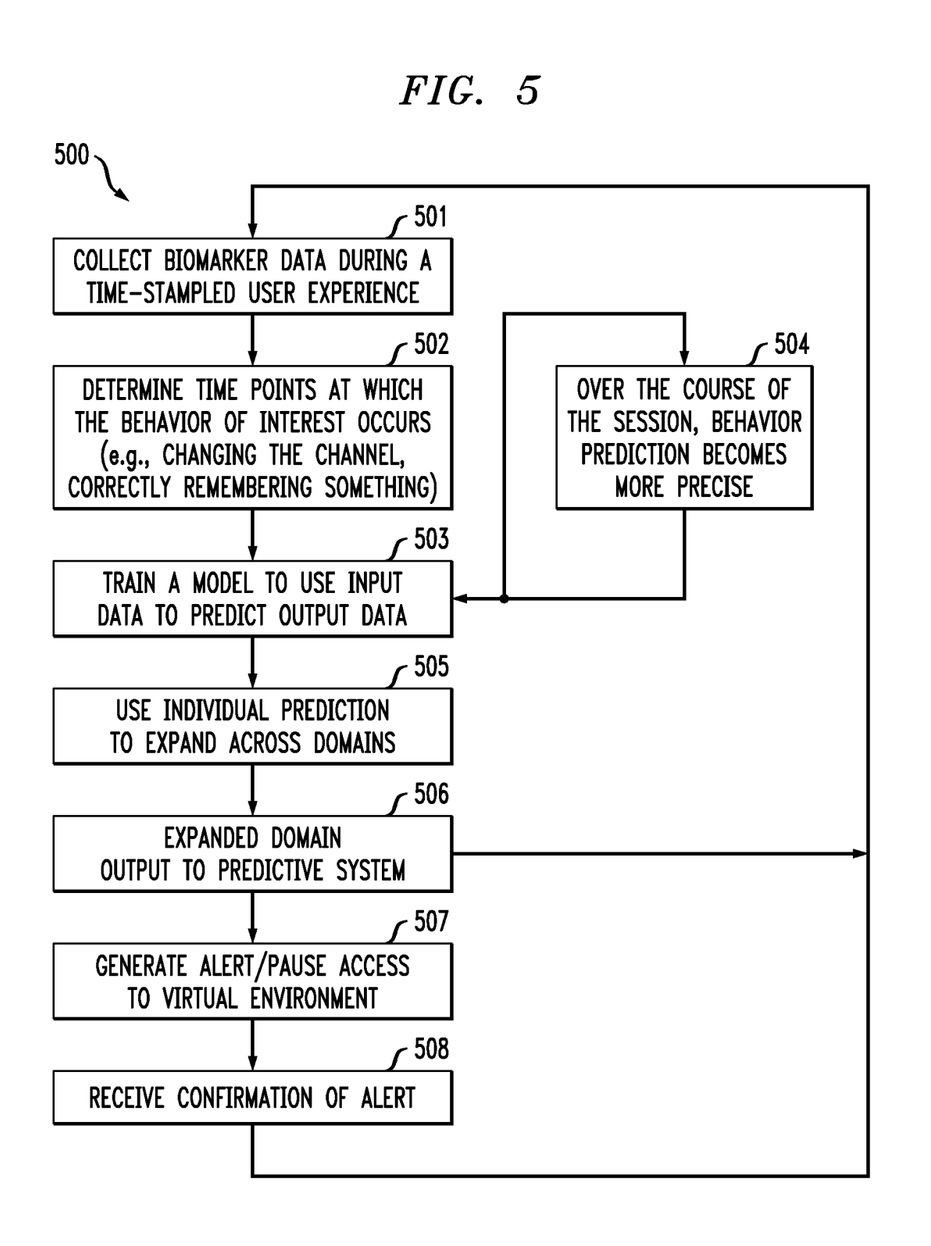
FIG. 5 is a flow diagram according to at least one embodiment of the present invention.

Referring to FIG. 5, according to some embodiments, a method 500 can include collecting biomarker data during a time-stamped process 501, determining time points at which the behavior of interest occurs 502, training a machine-learning system (iteratively 504) to use the biomarker data and behavior of interest to predict additional behavior 503, and using an individual prediction to expand across domains 505. At block 505, for example, a model used for purchasing equipment can inform a separate model used for purchasing clothes. According to one or more embodiments of the present invention, the expanded domain is output to a predictive system 506. In some embodiments, the predictive system provides feedback (e.g., an alert 507) to the method, for example, if the predictive system anticipates an event that increases a likelihood of a purchase or that diffuses a negative social interaction.

According to one or more embodiments of the present invention, a threshold of predictability of the response of the user is determined under a pre-determined context within the virtual environment. The context can be, for example, a degree of cooperation or aggression in a game, a purchase behavior given an advertisement or study, etc. Further, the system receives, during the sampling, output data from the sensors, detects in the output data that the threshold is satisfied and generating an alert to the virtual environment upon detecting that the threshold is satisfied.

According to some embodiments, the system requires the receipt of a confirmation from the user based on the alert to the virtual environment 508. In at least one embodiment, the user's access to the virtual environment is paused upon detecting that the threshold is satisfied 507.

According to one or more embodiments of the present invention, at block 507 the alert is transmitted to a remote device associated with an administrator account, such that the user's access to the virtual environment is resumed only once a confirmation is received from the remote device. According to at least one embodiment, the alert comprises a recorded portion of the interactions of the user within the virtual environment, such as interactions in a game, such that an administrator can effectively review the interactions on the remote device and disable the user's access of the virtual environment in a case where an interaction is not appropriate.

According to one or more embodiments of the present invention, the user's access to the virtual environment is paused upon detecting that the threshold is satisfied, and is resumed upon receipt of a confirmation from the remote device.

Exemplary implementations of one or more embodiments of the present invention can expand Watson Education and TSS offerings using machine learning to predict human behavior from biomarker data, add a closed-loop biofeedback mechanism in a therapeutic setting, such as Watson Health.

Figure 6:
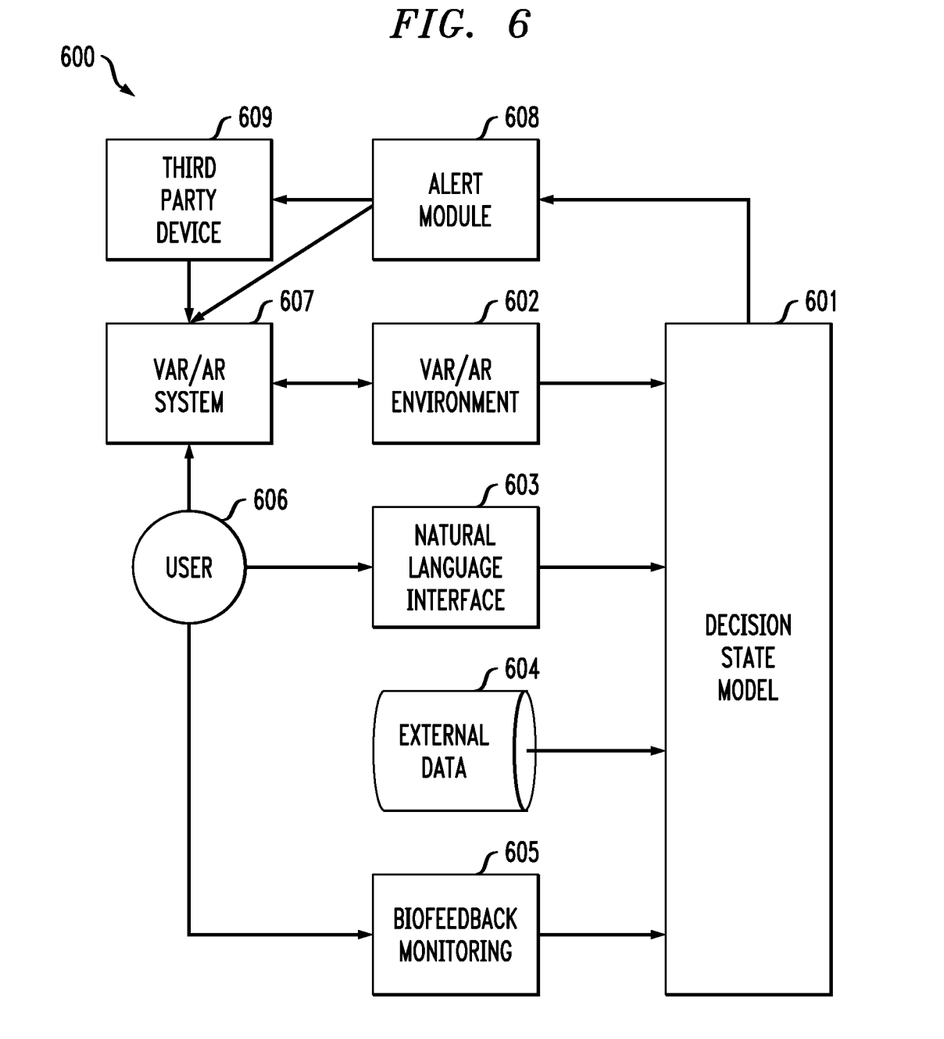
FIG. 6 is a flow diagram according to at least one embodiment of the present invention.

Referring to FIG. 6, according to some embodiments, a system 600 operating a user decision state model 601 receives input from one or more of a virtual environment 602, a natural language processing machine 603, an external database 604, and biofeedback monitors 605. The natural language processing machine 603 and biofeedback monitors 605 receive signals from a user 606. Furthermore, the virtual environment 602 is configured to process the activity of the user 606 through virtual reality (VR)/augmented reality (AR) systems 607. According to some embodiments of the system further comprises an alert module 608 for injecting alerts into the VR/AR environment 602 through the VR/AR system 607. According to one or more embodiments of the present invention, the alert is injected into a notification system of a third party device 609, such as an administrator's device; in this exemplary case, the user's access to the virtual environment is paused upon the alert being generated, and is resumed upon receipt of a confirmation from the third party device.

According to at least one embodiment of the present invention, the user is associated with an account that is mapped to contact information of the administrator, such that alerts can be transmitted to the administrator.

Figure 7:
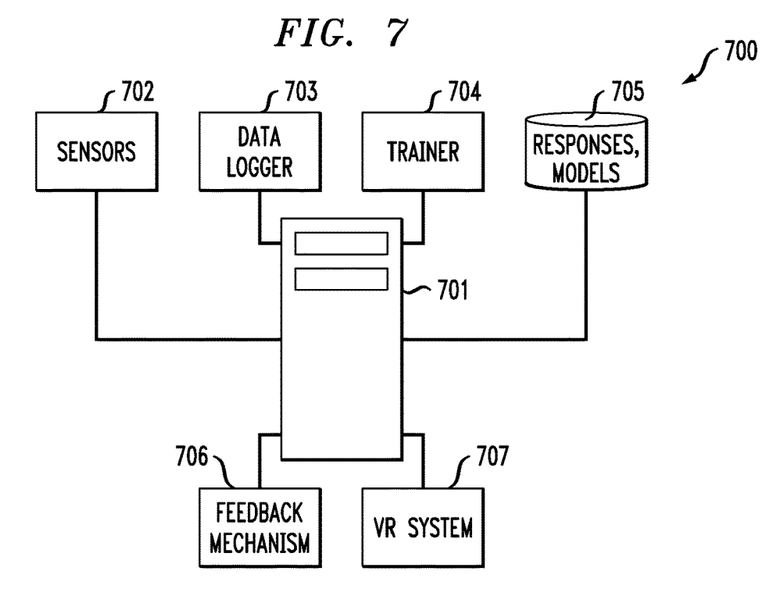
FIG. 7 is a diagram of a device according to at least one embodiment of the present invention.

Referring to FIG. 7, an exemplary system 700 comprises a computer system 701 including a user interface enabling a user to enter information (e.g., demographic variables). The system 700 comprises sensors 702 collecting biometric data. These sensors 702 can include cameras for eye tracking, a heart rate monitor, a respiration monitor etc. The sensors 702 enable the collection of time-stamped biometric data (e.g., skin conductivity, eye movements, facial muscle activity). The system 700 further includes a data logger 703 logging user behavior including for example, keystrokes, purchasing behavior, and psychometrics. The computer system 701 can include an application performing the functions of a trainer 704. The trainer 704 trains a time series model (e.g., impulse response filter, feed forward neural network, or predictive auto regression) to predict user behavior from the data made available by the sensors 702 and the data logger 703. The system 700 includes a database 705 storing the data made available by the sensors 702 and the data logger 703 and the models created by the trainer 704. The system 700 further includes a feedback mechanism 706 configured to output signals related to a predicted behavior. According to one or more embodiments of the present invention, the output signals are audio feedback and/or video feedback. According to another embodiment of the present invention, the feedback mechanism 706 can output data related to a predicted user intent, such as displaying an instruction or tip for performing a predicted action.

According to one or more embodiments of the present invention, the computer system 701 makes one or more of the models available to external systems including a VR system 707.

Referring again to FIG. 7 in connection with an exemplary implementation of embodiments of the present invention, a system including a laptop computer connecting a VR headset to multiple biosensors draws data from a user (e.g., directly in the case of pulse or indirectly based on observations of behavior). The VR headset is equipped with eye tracking functionality, and the connected biosensors collect pulse, GSR (skin conductance, a measure of autonomic function), and accelerometer data. The user uses the VR headset to participate in a social game in which individuals cooperate or compete to obtain resources in an interactive virtual environment to achieve a goal. As the individuals iteratively interact within the virtual environment and make decisions to pursue, trade, share, or otherwise obtain resources from one another, the system records biological information using the biosensors leading up to each outcome over the course of time. The VR system and its connected biofeedback sensors provides data to the system as input, and the user's ultimate social behavior (e.g., trade, share, etc.) serves as the output variable. The data provided to the system is logged (e.g., recorded in memory of the laptop computer) and fed to a training mechanism (e.g., unsupervised learning of a model) that links the user's biometric time course data to the output behavior. Over time, the model is updated, improving detection functionality, e.g., detection of changes in the feature space that allows the system to anticipate how a particular emotional/biological state predicts an outcome. For example, the model may learn that increases in heart rate and skin conductance, combined with changes in gaze, predict a chance of bartering resources (i.e., a particular user behavior). Alternatively, should the system anticipate a distinct patter that predicts an adversarial social interaction, it may alert the user 507 (e.g., through an on-screen text alert, an audio alert or a similar alert).

According to at least one exemplary embodiment, the system informs the user about detected predictive clues, which can be presenting to raise the user's attention to the current affective state or behavior, for example, enabling the user to decrease their own observable predictability to other users. These predictive clues can be presented as a visible or auditory alert produced through the VR system. According to at least one exemplary embodiment, the system displays an alert that must be acknowledged, e.g., by the user selecting a certain button, before a further interaction in the virtual environment can be completed.

According to one or more embodiments of the present invention, the alert is presented with a plurality of potential acknowledgments, e.g., acknowledged and confirmed, acknowledged and ignored, acknowledged and irrelevant. User acknowledgements can be input into training mechanism (e.g., a supervised learning method for the model), which can be used to improve alert generation.

Recapitulation:

According to at least one embodiment of the present invention, a system (700) includes a virtual reality system (707) configured to enable a user to interact with a virtual environment, a plurality of biofeedback sensors (702) configured to monitor a user, and a computer system (701) including a virtual reality module (607) configured to generate at least a view of the virtual environment, a biofeedback module (605) configured to fuse output of the plurality of biofeedback sensors, a training module (601) configured to generate a model of user behavior, wherein the training module executed by the computer system enables the computer system to make a prediction of a user response of the user using a corpus of biofeedback data, and an alert module (608) configured to generate at least one alert to the user via the virtual reality system based on the prediction.

According to some embodiments, a method of constructing a predictive model for user behavior in a virtual environment (200) comprises determining a baseline response for a plurality of sensors and an individual user (201), building an individualized model comprising a plurality of priors generated from the baseline responses (202), the individualized model configured to predict a response of the individual user based on a time-stamped stimulus presentation in the virtual environment, sampling, iteratively, responses of the user to respective events in the virtual environment during the presentation (203), linking each of the responses and the respective events to an interval of time (204), and updating at least one of the priors of the individualized model based on linked ones of the responses and events (205). Referring to block 204, linking includes aligning responses and events along a time course, which according to some embodiments is necessary to train and test a prediction. Accordingly, in some embodiments, responses and events are linked and the linked responses and events are used to predict a response at some time (t) in the future, e.g., at t=t+1.

According to at least one embodiment, the method further comprises predicting a behavior of the individual user based on a new event (505), and generating an alert to the virtual environment based on a predicted behavior of the individual user (507).

The methodologies of embodiments of the disclosure may be particularly well-suited for use in an electronic device or alternative system. Accordingly, embodiments of the present invention may take the form of an entirely hardware embodiment or an embodiment combining software and hardware aspects that may all generally be referred to herein as a "processor," "circuit," "module" or "system."

Furthermore, it should be noted that any of the methods described herein can include an additional step of providing a computer system operating a closed-loop machine learning system using multiple biomarkers to predict behavior specific to an individual. Further, a computer program product can include a tangible computer-readable recordable storage medium with code adapted to be executed to carry out one or more method steps described herein, including the provision of the system with the distinct software modules.

Figure 8:
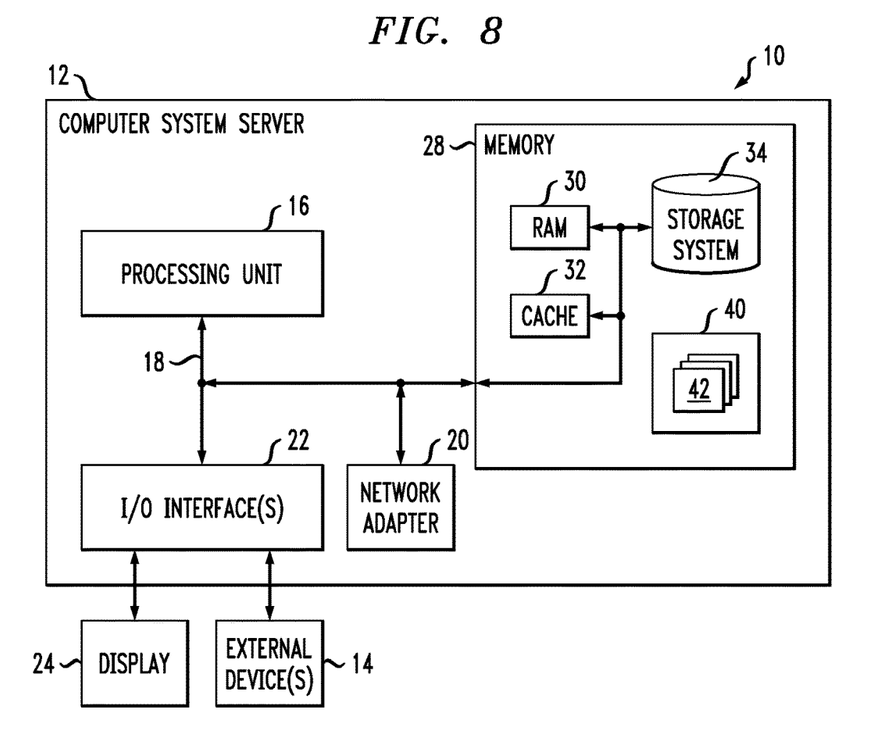
FIG. 8 depicts a computer system according to at least one embodiment of the present invention.

One or more embodiments of the invention, or elements thereof, can be implemented in the form of an apparatus including a memory and at least one processor that is coupled to the memory and operative to perform exemplary method steps. FIG. 8 depicts a computer system that may be useful in implementing one or more aspects and/or elements of the invention, also representative of a cloud computing node according to an embodiment of the present invention. Referring now to FIG. 8, cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 8, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 8, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 8) running a server program. It will be understood that such a physical server may or may not include a display and keyboard.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method of constructing a predictive model for user behavior in a virtual environment comprising:
   determining a baseline response for each of a plurality of sensors and a user;
   building an individualized model comprising a plurality of priors generated from the baseline responses, the individualized model configured to predict a given response of the user prior to the user starting a performance of the given response based on a time-stamped stimulus presentation in the virtual environment occurring after the building of the individualized model, wherein each of the priors is associated with a respective prediction and a plurality of baseline features in a feature space that is specific to the user and the prediction for an interval of time;
   sampling, iteratively, new responses of the user to respective events in the virtual environment during the time-stamped stimulus presentation, wherein respective intervals of times are determined for each of the new responses;
   linking each of the new responses and the respective events to respective ones of the intervals of time; and
   updating a first prior of the priors of the individualized model based on linked ones of the new responses and events, wherein updating the first prior comprises updating at least one value of the plurality of baseline features in the feature space of the first prior.

2. The method of claim 1, further comprising:
   predicting a future response of the user by determining a threshold of predictability of the given response of the user under a pre-determined context within the virtual environment;
   receiving, during the sampling, output data from the sensors;
   detecting in the output data that the threshold is satisfied; and
   generating an alert to the virtual environment upon detecting that the threshold is satisfied.

3. The method of claim 2, further comprising receiving a confirmation from the user based on the alert to the virtual environment.

4. The method of claim 2, further comprising pausing access of the user to the virtual environment upon detecting that the threshold is satisfied.

5. The method of claim 2, further comprising generating an alert, which is transmitted to a remote device.

6. The method of claim 5, further comprising:
   pausing access of the user to the virtual environment upon detecting that the threshold is satisfied; and
   resuming the access of the user to the virtual environment upon receipt of a confirmation from the remote device.

7. The method of claim 1, wherein updating the first prior further comprises updating a weight of the at least one value of the plurality of baseline features in the feature space of the first prior.

8. The method of claim 1, further comprising:
   generating a prediction of a future response of the user within the virtual environment, using the individualized model and the new responses of the user; and
   generating an alert to the virtual environment based on the prediction of the future response.

9. A non-transitory computer readable storage medium comprising computer executable instructions which when executed by a computer cause the computer to perform a method of constructing a predictive model for user behavior in a virtual environment, the method comprising:
   determining a baseline response for each of a plurality of sensors and a user;
   building an individualized model comprising a plurality of priors generated from the baseline responses, the individualized model configured to predict a given response of the user prior to the user starting a performance of the given response based on a time-stamped stimulus presentation in the virtual environment occurring after the building of the individualized model, wherein each of the priors is associated with a respective prediction and a plurality of baseline features in a feature space that is specific to the user and the prediction for an interval of time;
   sampling, iteratively, new responses of the user to respective events in the virtual environment during the time-stamped stimulus presentation, wherein respective intervals of times are determined for each of the new responses;
   linking each of the new responses and the respective events to respective ones of the intervals of time; and
   updating a first prior of the priors of the individualized model based on linked ones of the new responses and events, wherein updating the first prior comprises updating at least one value of the plurality of baseline features in the feature space of the first prior.

10. The computer readable storage medium of claim 9, further comprising:
    predicting a future response of the user by determining a threshold of predictability of the given response of the user under a pre-determined context within the virtual environment;
    receiving, during the sampling, output data from the sensors;
    detecting in the output data that the threshold is satisfied; and
    generating an alert to the virtual environment upon detecting that the threshold is satisfied.

11. The computer readable storage medium of claim 10, further comprising receiving a confirmation from the user based on the alert to the virtual environment.

12. The computer readable storage medium of claim 10, further comprising pausing access of the user to the virtual environment upon detecting that the threshold is satisfied.

13. The computer readable storage medium of claim 10, further comprising generating an alert, which is transmitted to a remote device.

14. The computer readable storage medium of claim 13, further comprising:
    pausing access of the user to the virtual environment upon detecting that the threshold is satisfied; and
    resuming the access of the user to the virtual environment upon receipt of a confirmation from the remote device.

15. The computer readable storage medium of claim 9, wherein updating the first prior further comprises updating a weight of the at least one value of the plurality of baseline features in the feature space of the first prior.

16. The computer readable storage medium of claim 9, further comprising:
    generating a prediction of a future response of the user within the virtual environment, using the individualized model and the new responses of the user; and
    generating an alert to the virtual environment based on the prediction of the future response.

* * * * *